US012661482B2

(12) United States Patent
Nelson et al.

(10) Patent No.: US 12,661,482 B2
(45) Date of Patent: Jun. 23, 2026

(54) STEERABLE MEMBER AND SYSTEM AND METHODS OF MAKING AND USING SAME

(71) Applicants: BOSTON SCIENTIFIC SCIMED, INC., Maple Grove, MN (US); MAYO FOUNDATION FOR MEDICAL EDUCATION AND RESEARCH, Rochester, MN (US)

(72) Inventors: Mitchell Nelson, Hudson, WI (US); Jason John Matteson, Jr., Beldenville, WI (US); Matthew Maciej, Rogers, MN (US)

(73) Assignees: BOSTON SCIENTIFIC SCIMED, INC., Maple Grove, MN (US); MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 463 days.

(21) Appl. No.: 18/138,687

(22) Filed: Apr. 24, 2023

(65) Prior Publication Data

US 2023/0338709 A1 Oct. 26, 2023

Related U.S. Application Data

(60) Provisional application No. 63/334,601, filed on Apr. 25, 2022.

(51) Int. Cl.
| | |
|---|---|
| A61M 25/01 | (2006.01) |
| A61M 25/00 | (2006.01) |
| A61B 17/00 | (2006.01) |

(52) U.S. Cl.
CPC ...... A61M 25/0147 (2013.01); A61M 25/005 (2013.01); *A61B 2017/00327* (2013.01)

(58) Field of Classification Search
CPC ............ A61M 25/0147; A61M 25/005; A61M 2025/015; A61B 2017/00327
See application file for complete search history.

(56) References Cited

U.S. PATENT DOCUMENTS

| | | | |
|---|---|---|---|
| 2004/0122360 A1* | 6/2004 | Waldhauser | ........ A61M 25/005 264/234 |
| 2012/0277671 A1 | 11/2012 | Fuentes | |

(Continued)

FOREIGN PATENT DOCUMENTS

| | | |
|---|---|---|
| JP | 2012016416 A | 1/2012 |
| JP | 2022507270 A | 1/2022 |

(Continued)

OTHER PUBLICATIONS

International Search Report and Written Opinion for International Application No. PCT/US2023/019684, mailed Sep. 13, 2023.

*Primary Examiner* — Richard G Louis
(74) *Attorney, Agent, or Firm* — Seager, Tufte & Wickhem, LLP

(57) ABSTRACT

A steerable device and system allowing a steerable elongate member positioned within another steerable tubular elongate member to be steered independently of the steerable tubular elongate member. The steerable tubular elongate member may be steered in a first plane, bending the steerable elongate member therein in the first plane as well. A steering mechanism operatively associated with the steerable elongate member has a distal portion operatively associated with a steerable region of the steerable elongate member to steer such steerable region within a second plane transverse to the first plane. The steering mechanism is independently movable with respect to a portion of the steerable elongate member proximal to the steerable region so as not to affect (Continued)

the orientation of the steerable region to be steered into a second plane transverse to the first plane.

15 Claims, 4 Drawing Sheets

(56)                   References Cited

U.S. PATENT DOCUMENTS

| | | | |
|---|---|---|---|
| 2015/0174363 A1* | 6/2015 | Sutermeister ....... | A61M 25/005 |
| | | | 604/95.04 |
| 2016/0158497 A1* | 6/2016 | Tran ................. | A61M 25/0071 |
| | | | 604/95.04 |
| 2022/0040453 A1* | 2/2022 | Johnson ................ | B29C 64/295 |
| 2023/0011214 A1 | 1/2023 | Nelson et al. | |

FOREIGN PATENT DOCUMENTS

| | | | |
|---|---|---|---|
| WO | 20201020389 A1 | 5/2020 | |
| WO | 2021217242 A1 | 11/2021 | |

* cited by examiner

STEERABLE MEMBER AND SYSTEM AND METHODS OF MAKING AND USING SAME

CROSS-REFERENCE TO RELATED APPLICATIONS

This application claims the benefit of priority of U.S. Provisional Application No. 63/334,601, filed Apr. 25, 2022, the entire disclosure of which is hereby incorporated by reference herein for all purposes.

FIELD

The present disclosure relates generally to the field of medical devices and systems. More particularly, the present disclosure relates to steerable devices and systems, typically including elongate members such as catheters, and methods of using and making same.

BACKGROUND

Devices, systems, and methods for delivering and/or deploying medical devices with minimally invasive techniques, such as percutaneously and/or transluminally, are desirable for avoiding more complex and invasive open surgical procedures. Various techniques which do not require open surgery utilize systems and devices with various flexible elongate members capable of navigating to an anatomical site within the body from a small insertion opening in a patient's body, transluminally through the body (such as through the vascular system), and to an anatomical site. A wide variety of intracorporeal medical devices have been developed for transluminal medical use, for example, intravascular use. Some of these systems and devices include guidewires, catheters, medical device delivery systems (e.g., for implantable devices such as tissue anchors, stents, grafts, replacement valves, etc.), and the like. Such systems may be multi-catheter/stacked catheter assemblies which include a plurality of tubular elongate members stacked one within the other (coaxially and/or coextensively within another flexible tubular elongate member). One or more such devices may be independently steerable through the body and to a desired anatomical site. However, if an outer tubular elongate member is bent, elongate members generally therein bend with such outer tubular elongate member. More particularly, inner elongate members within the outer tubular elongate member will follow the bend in the outer bent steerable flexible tubular elongate member, specifically the shortest path, and thus migrate to the inner region of the bend (i.e., on the inner curve, closer to an imaginary point or axis about which the members bend). Any steering mechanism of such inner elongate member typically will also follow a bend in the outer tubular elongate member, and will also shift or migrate to the shortest path of the bend. If the steering mechanism extends longitudinally along only a section of (i.e., not extending completely around) the circumference of the inner elongate member, the steering mechanism will torque the steerable region of the inner elongate member with which it is coupled. Such torquing or realignment of the steering mechanism may interfere with later control of such steering mechanism to navigate at least the steerable region of the inner elongate member to a desired anatomical site. Improvements to steering mechanisms of elongate members navigated within steerable outer tubular elongate members would thus be welcome in the art.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a steerable system for accessing an anatomical site within a patient's body includes an elongate member having a steerable region along a portion thereof, and a steering mechanism having a distal portion operatively associated with the steerable region to effect movement of the steerable region, and a proximal portion axially and radially movable with respect to the steerable region.

In some embodiments, the distal portion of the steering mechanism is embedded within a distal portion of the elongate member. In some embodiments, the steering mechanism comprises a two-part pull mechanism with an inner pull wire axially movable within an outer sheath, a portion of the outer sheath is fixed with respect to the steerable region of the elongate member; and a distal end of the pull wire is coupled to the outer sheath such that axial movement of the pull wire steers the outer sheath.

In some embodiments, the elongate member has a tubular wall defining a lumen therein, the distal portion of the steering mechanism is operatively associated with the tubular wall of the flexible elongate member along the steerable region to steer the steerable region, and the proximal portion of the steering mechanism extends within the lumen defined by the tubular wall of the elongate member and is movable radially-independently of the steerable region. In some embodiments, the tubular wall of the elongate member comprises an outer layer, an inner layer, and a reinforcing layer therebetween, the steering mechanism being operatively associated with one of the layers of the tubular wall. In some embodiments, the steering mechanism is operatively associated with the reinforcing layer. In some embodiments, the reinforcing layer comprises a plurality of woven filaments, and the distal portion of the steering mechanism is interwoven with the woven filaments of the reinforcing layer. In some embodiments, the steering mechanism comprises a two-part pull mechanism with an inner pull wire axially movable within an outer sheath, a portion of the outer sheath is operatively associated with filaments of the reinforcing layer along the steerable region, and a distal end of the pull wire is coupled to the outer sheath such that axial movement of the pull wire steers the steerable region. In some embodiments, the portion of the outer sheath operatively associated with the filaments along the steerable region is fixed with respect to the steerable region.

In some embodiments, a distal end of the steering mechanism is fixed with respect to the steerable region.

In accordance with various principles of the present disclosure a steerable system comprises at least one steerable tubular member, an inner steerable member extending through and along the at least one steerable tubular member and having a steerable portion along a distal end thereof, and a steering mechanism having a distal portion operatively associated with the steerable region of the inner steerable member to effect movement of the steerable region, and a proximal portion radially movable with respect to the steerable region, wherein the at least one steerable tubular member is steered within a first plane and the steering mechanism is operatively associated with the inner steerable member to steer the inner steerable member in a second plane transverse to the first plane.

In some embodiments, the at least one steerable tubular member includes a two-way steerable delivery catheter, and the inner steerable member is axially extendable out of a distal end of the two-way steerable delivery catheter and steered by the steering mechanism within the second plane.

In some embodiments, the inner steerable member has a tubular wall defining a lumen therein, the distal portion of the steering mechanism is operatively associated with the tubular wall of the inner steerable member along the steerable region to steer the steerable region; and the proximal portion of the steering mechanism extends within the lumen defined by the tubular wall of the inner steerable member and is movable radially-independently of the steerable region. In some embodiments, the tubular wall of the inner steerable member comprises an outer layer, an inner layer, and a reinforcing layer therebetween, the steering mechanism being operatively associated with one of the layers of the tubular wall. In some embodiments, the reinforcing layer comprises a plurality of woven filaments, and the distal portion of the steering mechanism is interwoven with the woven filaments of the reinforcing layer. In some embodiments, the steering mechanism comprises a two-part pull mechanism with an inner pull wire axially movable within an outer sheath, a portion of the outer sheath is operatively associated with filaments of the reinforcing layer along the steerable region; and a distal end of the pull wire is fixed to the outer sheath such that axial movement of the pull wire steers the steerable region. In some embodiments, the portion of the outer sheath operatively associated with the filaments along the steerable region is fixed with respect to the steerable region.

In some embodiments, a distal end of the steering mechanism is fixed with respect to the steerable region.

In accordance with various principles of the present disclosure, a method of navigating a steerable delivery/deployment system with respect to a steerable delivery catheter includes bending the steerable tubular delivery catheter and thus the steerable delivery/deployment system within a first plane to deliver the steerable delivery/deployment system to an area of an anatomical site; and operating a steering mechanism to steer a steerable region of the steerable delivery/deployment system within a second plane transverse to the first plane, the steering mechanism having a distal portion fixed with respect to the steerable region to steer the steerable region, and a proximal portion radially movable with respect to the steerable region to conform to the bend of the steerable delivery catheter in the first plane.

In some embodiments, the method further includes allowing the proximal portion of the steering mechanism to conform to the bend of the steerable delivery catheter without torquing the steerable region of the steerable delivery/deployment system out of position to be bent in the second plane by the steering mechanism.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. It will be appreciated that common features are identified by common reference elements and, for the sake of brevity and convenience, and without intent to limit, the descriptions of the common features are generally not repeated. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
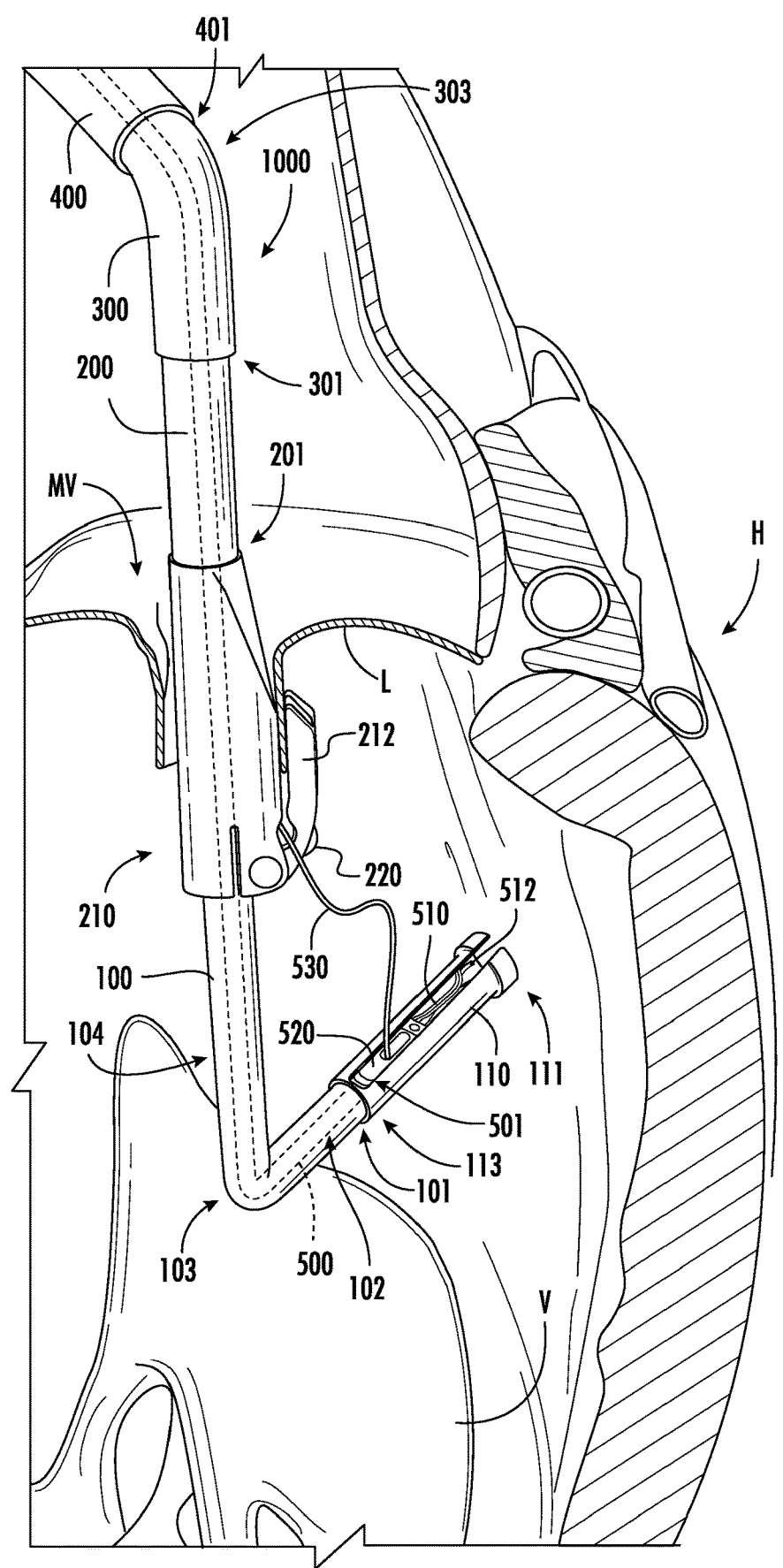
FIG. 1 illustrates a perspective view of an example of an embodiment of a steerable system formed in accordance with various principles of the present disclosure shown in a schematic representation of a heart.
Figure 2:
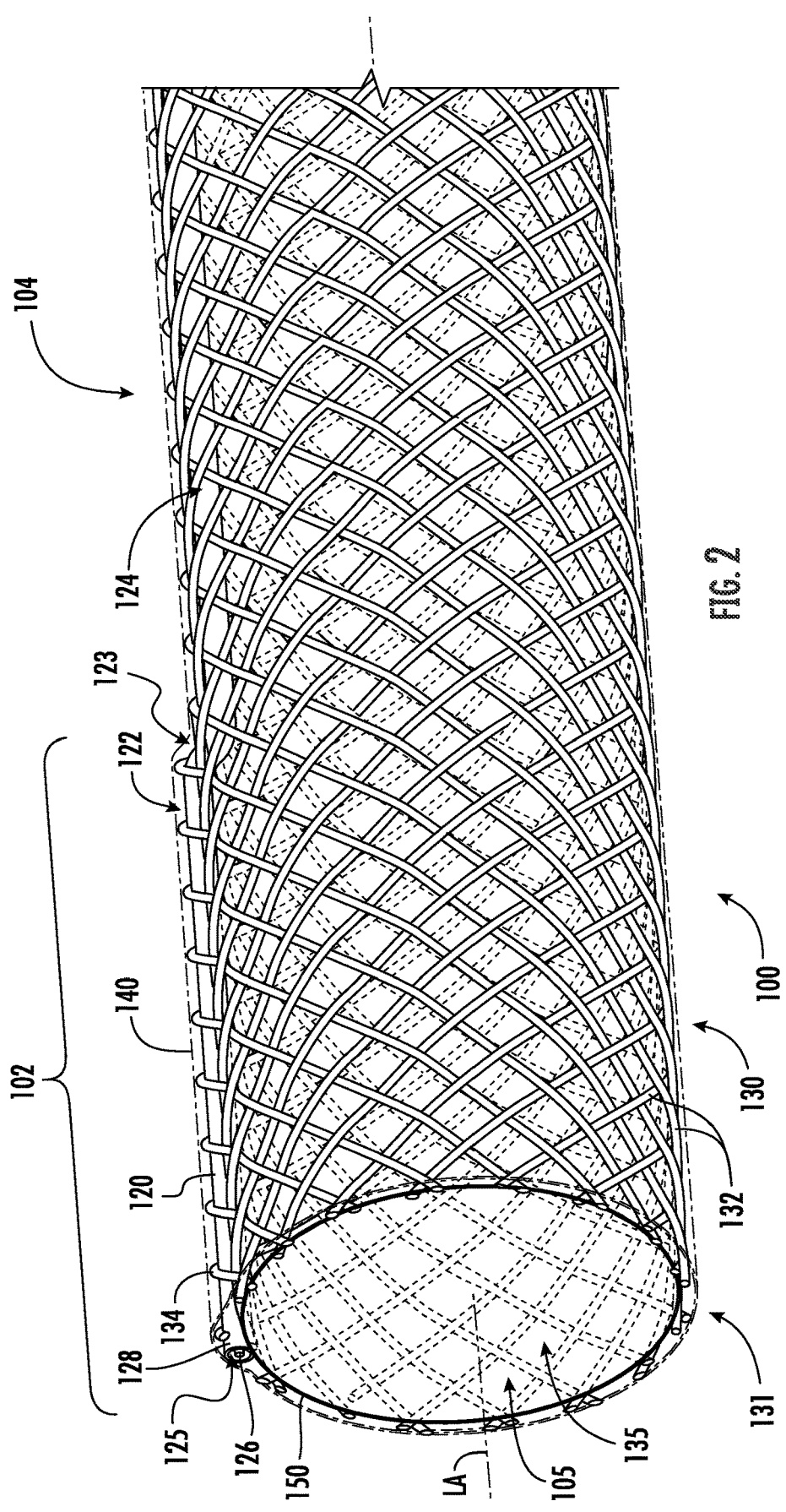
FIG. 2 illustrates a perspective view of a portion of a steerable flexible tubular elongate member with an outer layer thereof shown in phantom.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and/or closest to a delivery device, and "distal" refers to the direction or location furthest from the user, such as when using the device (e.g., introducing the device into a patient, or during implantation, positioning, or delivery), and/or closest to a delivery device. "Longitudinal" means extending along the longer or larger dimension of an element. A "longitudinal axis" extends along the longitudinal extent of an element, though is not necessarily straight and does not necessarily maintain a fixed configuration if the element flexes or bends. "Central" means at least generally bisecting a center point and/or generally equidistant from a periphery or boundary, and a "central axis" means, with respect to an opening, a line that at least generally bisects a center point of the opening, extending longitudinally along the length of the opening when the opening comprises, for example, a tubular element, a strut, a channel, a cavity, or a bore. As used herein, a "channel" or "bore" is not limited to a circular cross-section. As used herein, a "free end" of an element is a terminal end at which such element does not extend beyond. It will be appreciated that terms such as engage (and other grammatical forms thereof) may be used interchangeably herein with terms such as couple, grasp, hold, clasp, clip, anchor, attach, affix, secure, etc. (and other grammatical forms thereof), without intent to limit, and include direct and indirect engagement unless otherwise indicated. It will be appreciated that terms such as portion, area, section, segment, etc., may be used interchangeably herein without intent to limit unless otherwise indicated. It will be appreciated that terms such as procedures, operations, therapies, treatments, diagnostics, etc. (including all grammatical forms thereof) may be used interchangeably herein without intent to limit. Reference may be made to an anatomical site, delivery site, deployment site, implant/ implantation site, target site, treatment site, etc., interchangeably and without intent to limit.

Accessing regions within a body without cutting open the body (i.e., accessing such regions transluminally) often requires steering an elongate member into a complex position. For example, a procedure may involve navigating the elongate member in multiple directions, such as within a first plane and then within a second plane transverse to the first plane, and even within additional third, fourth, fifth, etc., planes. Various procedures such as, and without limitation, mitral valve therapies, utilize systems with more than one steerable elongate member, such as telescoped and/or stacked one within the other (coaxially and/or side-by-side and optionally within another tubular elongate member). The elongate members of such systems may need to be steered independently within different planes transverse to one another. For instance, an outer steerable tubular elongate member (such as a delivery catheter) may be steered in one or more planes to position a distal end of the steerable system at an anatomical site at which a procedure is to be performed with the use of such steerable system. A distal portion of the outer steerable tubular elongate member may be steered and/or bent in a delivery plane for the system to place another system or device in a desired position with respect to the anatomical site (for instance, to center the distal end of the system on the mitral valve for repairing the mitral valve with another system or device). The other system or device may be delivered and/or deployed by an inner steerable elongate member extending within the outer steerable tubular elongate member and which is telescoped out of the outer tubular elongate member and then steered into another position. For instance, the inner steerable elongate member may be bent in a plane transverse to the delivery plane in which the outer tubular elongate member generally remains bent to maintain the distal end thereof in position for initial delivery of the other system or device by the inner steerable elongate member.

As may be appreciated in view of basic physics, the configuration of the outer steerable tubular elongate member biases and influences the configuration of elongate members therein. For instance, a bend in the steerable tubular elongate member causes elongate members therein to be pulled and driven and biased to the inside of the bend radius of the outer steerable elongate member to take the shortest path along the bend. As such, the outer steerable tubular elongate member predefines a plane in which elongate members therein can articulate. An inner steerable elongate member delivered by the outer steerable tubular elongate member to deliver or deploy a further system or device thus may have limited ability to steer out of the delivery plane of the outer steerable tubular elongate member and to be torqued relative to the outer steerable tubular elongate member, such as to be bent into or within another plane. For example, steerable elongate members may utilize one or more steering mechanisms coupled to a steerable region of a respective steerable elongate member. Such steering mechanism generally is coupled along a portion of the circumference of the steerable elongate member to cause the steerable elongate member to bend in the direction of the area at which the steering mechanism is coupled. For instance, if two or more steering mechanisms are used, such steering mechanisms typically are circumferentially spaced apart from each other, such as extending along opposite sides of the steerable elongate member, to control bending of the elongate member in opposite directions. To steer the steerable elongate member, the steering mechanism is actuated (e.g., pulled), causing the associated steerable region of the steerable elongate member to bend/flex, generally towards the area at which the steering mechanism is coupled with the steerable region of the steerable elongate member. The area at which the steerable region is coupled with the steering mechanism will be driven to the inside of the bend radius of the steerable region to take the shortest path. However, any steering mechanism of a steerable elongate member bent within an already-bent outer steerable tubular elongate member will align with the bends of the steerable elongate member and the outer steerable tubular elongate member. Specifically, the steering mechanism will be pulled by the bend in the outer steerable elongate member and being driven and biased to the inside of the radius of such bends to take the shortest path along the bend. Such alignment of the steering mechanism will torque the area at which the steering mechanism is coupled with the steering region of the steerable elongate member. With the steerable region pulled into such position, steering of the inner elongate member with a standard steering mechanism would face challenges when attempted to be steered out of the plane in which the outer steerable tubular elongate member is bent. For some therapies, the inner steerable elongate member must be capable of being steered out of the plane in which it is delivered by an outer steerable tubular elongate member, such as to access the anatomical regions to be treated.

Principles of the present disclosure may be applied to various systems with at least one steerable elongate member within another steerable tubular elongate member. Such steerable elongate members typically are flexible, either by nature of the material thereof or as a result of articulations formed therein. For the sake of convenience, and without intent to limit, reference may be made herein to a delivery/deployment system with more than one steerable elongate member delivering and/or deploying a medical device and/or system. However, it will be appreciated that principles of the present disclosure may be applied to systems other than those for delivery and/or deployment of a medical device and/or system. It will be appreciated that the term elongate member or tubular elongate member is used herein generically to refer to elements such as catheters, shafts, cannulas, sheaths, tubes, stylets, etc., for the sake of convenience and without intent to limit. Moreover, it will be appreciated that terms such as steer (and other grammatical forms thereof) may be used interchangeably herein with such terms (and other grammatical forms thereof) as actuate, articulate, control, maneuver, manipulate, move, navigate, operate, shift, transition, drive, advance, pull, retract, rotate, translate, etc., without intent to limit.

In accordance with various principles of the present disclosure, a steerable system includes at least one outer steerable tubular elongate member and at least one inner steerable elongate member, such as inner steerable tubular elongate member. Although various embodiments may be described herein with reference to a tubular inner steerable elongate member, principles of the present disclosure being applicable to steerable elongate members which are not necessarily tubular/hollow. For the sake of simplicity and brevity, and without intent to limit, reference is generally made simply to an outer steerable member and an inner steerable member, with the understanding that such members are generally elongate, optionally (and generally advantageously) also flexible, and optionally (and generally advantageously) also tubular. The outer steerable member may be steered in one or more directions within one or more planes, such as with the use of a steering mechanism such as a pull mechanism. The inner steerable member is configured in accordance with various principles of the present disclosure to be steerable independently of the outer steerable member, such as in a different steering plane (e.g., if the outer steerable member is bent within a first plane, then the inner steerable member is capable of bending in another plane transverse to the first plane). In some aspects, a steering mechanism is coupled to a portion of the inner steerable member to bend or otherwise manipulate the inner steerable member in a desired direction so that the inner steerable member may be navigated in a desired direction, independently of the outer steerable member (e.g., without being influenced by, such as pulled in the direction of, a bend in the outer steerable member in which the inner steerable member extends). The portion of the inner steerable member to which the steering mechanism is operatively engaged is typically along a distal region of the inner steerable member, though need not be so limited. For the sake of convenience, and without intent to limit, the region of the inner steerable member steered by (e.g., bent by) the steering mechanism is operatively engaged is referenced herein as a steerable region.

In some embodiments, the steering mechanism is operatively associated with (e.g., coupled or engaged with to operate) a portion of the wall of the inner steerable member along a steerable region of the inner steerable member in any of a variety of manners to effect movement of the steerable region, such as by pulling or otherwise manipulating the steering mechanism. The steering mechanism may be coupled to a portion of the wall of the inner steerable member such as by being adhered, bonded, welded, etc., to or within (e.g., embedded within) a portion of the wall of the inner steerable member. In some embodiments, the steering mechanism is a pull mechanism such as a pull element. In some embodiments, the pull mechanism is a two-part mechanism, such as a Bowden cable, with an outer tubular sheath and an inner pull element such as a flexible elongate pull element (e.g., a pull wire). The outer tubular sheath allows movement of the inner pull element relative to the inner steerable member to steer the inner steerable member even if the outer tubular sheath is fixed with respect to the inner steerable member (such as to fix, or as a result of operatively associating, the steering mechanism with respect to the inner steerable member). Generally, the distal end of the inner pull element is fixed to the outer tubular sheath (which is, in turn, fixed with respect to the inner steerable member) so that proximal pulling of the inner pull element pulls the steerable region of the inner steerable member to move the inner steerable member as desired.

Other manners of operatively associating a steering mechanism with a steerable member so that manipulation of a proximal end of the steering mechanism effects movement of a steerable region of the steerable member in a desired manner are within the scope and spirit of the present disclosure. For instance, instead of a steering mechanism extending along the entire length of a steerable region, the steerable region may be stiffer than adjoining regions of the steerable member. The steering mechanism need only be operatively engaged with the proximal end or area of the stiffened steerable region to be able to steer such stiffened steerable region (e.g., pulling on a proximal area of such stiffened steerable region will cause the entire stiffened steerable region to bend).

It may be desirable to allow an inner steerable member within an outer steerable member of a steerable system to be steered in a plane different from the plane in which the outer steerable member is positioned. In other words, it may be desirable for an inner steerable member, within an outer steerable member bent in a first plane, to be steered out of such first plane. Such first plane may be a delivery plane in which the outer steerable member delivers the inner steerable member to a general anatomical area, the inner steerable member being further navigated therefrom to a particular anatomical site in a plane transverse to the delivery plane of the outer steerable member. In accordance with various principles of the present disclosure, to allow steering of an inner steerable member independent of an outer steerable member (in which the inner steerable member extends), even if the outer steerable member (and thus at least a portion of the inner steerable member) is bent within a first plane, the steering mechanism of the inner steerable member is coupled to only the steerable region of the inner steerable member. The portion of the steering mechanism proximal to the steerable region is freely movable at least radially with respect to the inner steerable member, such as within or into the first plane. For instance, a steering mechanism of a tubular inner steerable member is coupled to only the steerable region of such tubular inner steerable member (e.g., a distal portion of the tubular wall of the inner steerable member), and the portion of the steering mechanism proximal to such steerable region is movable radially with respect to the steerable region. In some embodiments, the proximal portion of the steering mechanism is movable within a lumen defined by the tubular wall of a tubular inner steerable member. In some embodiments, the steering mechanism is operatively associated with an inner steerable member only at a distal region or extent of the inner steerable member. The remainder of the steering mechanism proximal to the steerable region of the inner steerable member is independently movable, at least radially, with respect to the steerable region so that such proximal portion of the steering mechanism may follow the inner bend of the inner steerable member without affecting (e.g., torquing) the distal portion of the steering mechanism operatively associated with the steerable region of the inner steerable member. The proximal portion of the steering mechanism (e.g., lying within the first plane) is dissociated from the inner steerable member so as not to affect the orientation of the steerable region to be able to be steered into a second plane transverse to the first plane. In other words, because the steering mechanism is fixed with respect to only the steerable region, and is not fixed along the longitudinal extent of the inner steerable member proximal to the steerable region, the steerable region is not torqued by a proximal portion of the steering mechanism (not itself fixed with the inner steerable member) being pulled toward the inside of a bend radius of a bent outer steerable member in which the inner steerable member is positioned and also bent.

A steering mechanism formed in accordance with various principles of the present disclosure is capable of manipulating the steerable region without being affected by regions of the steering mechanism proximal to the steerable region. In some embodiments, the portion of the steering mechanism which is operatively associated with the inner steerable member defines the steerable region of the inner steerable member. For instance, in accordance with various principles of the present disclosure a steering mechanism in the form of a pull mechanism is capable of steering the portion of the inner steerable member with which the pull mechanism is substantially fixed against radial movement (in contrast with a portion of the inner steerable member with respect to which the pull mechanism is freely radially movable). In some instances, a steering mechanism may be a two-part pull mechanism having an outer sheath with a portion by which the steering mechanism is coupled to the steerable region of an inner steerable member to effect steering movement (e.g., a portion fixed and not movable with respect to the steerable region). The inner pull element is generally movable (at least longitudinally movable) with respect to such generally radially fixed extent of the outer sheath. Because the distal end of the inner pull element is coupled to the outer sheath of the pull mechanism, manipulation (e.g., pulling) of the inner pull element moves the outer sheath and thus the steerable region of the inner steerable member coupled thereto. Because the steering mechanism proximal to the steerable region is freely movable radially with respect to the inner steerable member, movement of the inner steerable member caused by movement of the steering mechanism (e.g., the inner pull element) is limited to the steerable region. As such, the extent of the outer sheath coupled with the inner steerable member may be considered to define the steerable region of the inner steerable member. The portion of the steering mechanism proximal to the steerable region moves independently of the inner steerable member such that the portion of the inner steerable member proximal to the steerable region is unaffected by movement of the steering mechanism (e.g., is not manipulated or otherwise by movement of the steering mechanism). It will be appreciated that the outer sheath as well as the inner pull element of the described example of an embodiment of a two-part steering mechanism generally are movable independently of the inner steerable member proximal to the steerable region.

It will be appreciated that an independently steerable inner steerable member within an outer steerable member of a steerable system may be useful in a variety of steerable systems for a variety of methods of operation or use. For the purpose of the present disclosure, the descriptions of examples of embodiments provided below reference treatment of a native mitral valve for the sake of convenience to provide an example of an environment in which principles of the present disclosure may be applied. However, those of ordinary skill in the art may readily appreciate that principles of the present disclosure may be applied to another heart valve or region of the heart or another anatomical region altogether with no or minimal changes to the structure and/or scope of the steering mechanisms and/or steerable members of the present disclosure. For instance, devices, systems, and methods disclosed herein may have applications and uses in other portions of a patient's anatomy, such as but not limited to, arteries, veins, and/or other body lumens or organs.

Various embodiments of a steerable member, system, and associated methods of formation and use, will now be described with reference to examples illustrated in the accompanying drawings. Reference in this specification to "one embodiment," "an embodiment," "some embodiments", "other embodiments", etc. indicates that one or more particular features, structures, concepts, and/or characteristics in accordance with principles of the present disclosure may be included in connection with the embodiment. However, such references do not necessarily mean that all embodiments include the particular features, structures, concepts, and/or characteristics, or that an embodiment includes all features, structures, concepts, and/or characteristics. Some embodiments may include one or more such features, structures, concepts, and/or characteristics, in various combinations thereof. It should be understood that one or more of the features, structures, concepts, and/or characteristics described with reference to one embodiment can be combined with one or more of the features, structures, concepts, and/or characteristics of any of the other embodiments provided herein. That is, any of the features, structures, concepts, and/or characteristics described herein can be mixed and matched to create hybrid embodiments, and such hybrid embodiment are within the scope of the present disclosure. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. It should further be understood that various features, structures, concepts, and/or characteristics of disclosed embodiments are independent of and separate from one another, and may be used or present individually or in various combinations with one another to create alternative embodiments which are considered part of the present disclosure. Therefore, the present disclosure is not limited to only the embodiments specifically described herein, as it would be too cumbersome to describe all of the numerous possible combinations and subcombinations of features, structures, concepts, and/or characteristics, and the examples of embodiments disclosed herein are not intended as limiting the broader aspects of the present disclosure. The following description is of illustrative examples of embodiments only, and is not intended as limiting the broader aspects of the present disclosure.

Turning now to the drawings, it will be appreciated that common features are identified by common reference elements and, for the sake of brevity and convenience, and without intent to limit, the descriptions of the common features are generally not repeated. For purposes of clarity, not all components having the same reference number are numbered. Moreover, a group of similar elements may be indicated by a number and letter, and reference may be made generally to one or such elements or such elements as a group by the number alone (without including the letters associated with each similar element). It will be appreciated that, in the following description, elements or components similar among the various illustrated embodiments are generally designated with the same reference numbers and redundant description may generally be omitted for the sake of brevity. Moreover, certain features in one embodiment may be used across different embodiments and are not necessarily individually labeled when appearing in different embodiments.

Principles of the present disclosure may be applied to a steerable member 100 used in an example of an embodiment of a system such as a multi-catheter stack-up assembly 1000 such as illustrated in FIG. 1. Although the multi-catheter stack-up assembly 1000 (alternately referenced herein as a system 1000 for the sake of simplicity) is illustrated in an example environment of a heart, it will be appreciated that other environments are within the scope and spirit of the present disclosure. Principles of the present disclosure are particularly useful in devices and systems for accessing an anatomical site within a patient's body via a transluminal access within the body and without cutting open the body.

A steerable member 100 to which principles of the present disclosure may be applied is illustrated as extending through (and projected distally outwardly from the distal end 201 of) another, optional, device catheter 200, both of which extend within, through, and out a distal end 301 of a delivery catheter 300. The delivery catheter 300, in turn, extends within, through, and out a distal end 401 of a delivery sheath 400. The steerable member 100 may assist with delivering a further device (such as an implantable device 510) delivered on or at the distal end 501 of a stylet 500 extending through the inner steerable member 100. The steerable member 100 is referenced herein as an inner steerable member 100 to distinguish from other elongate members in which the inner steerable member 100 extends. The illustrated example of an embodiment of an inner steerable member 100 may be flexible and elongate and thus may also be referenced herein as a steerable flexible elongate member 100. One or more of the flexible tubular elongate members 200, 300, 400 may be steerable as well. As may be appreciated, the positions in which one or more of the flexible tubular elongate members 200, 300, 400 extend typically affect the position of the inner steerable member 100 which extends therein. For instance, a bend in one or more of the flexible tubular elongate members 200, 300, 400 may bend the inner steerable member 100 in a similar direction. In accordance with various principles of the present disclosure, a steering mechanism is operatively associated with the inner steerable member 100 to steer at least a steerable region 102 of the inner steerable member 100 within a plane different from the plane in which the flexible tubular elongate members 200, 300, 400 lie (e.g., by virtue of a bend in a steerable tubular elongate member, such as flexible tubular elongate member 300, in which the inner steerable member 100 extends). An example of an embodiment of a steering mechanism 120 which may steer the inner steerable member 100 in a manner as illustrated in FIG. 1 is illustrated in FIG. 2, FIG. 3, FIG. 4, and FIG. 5, as discussed in further detail below.

In the example of an embodiment of a multi-catheter stack-up assembly 1000 illustrated in FIG. 1, the outermost of the illustrated flexible tubular elongate members 200, 300, 400 may be a delivery guide sheath 400 (also known as an introducer) introduced into the body with a dilator (not shown, but which may be any known dilator), such as through the femoral artery to cross through the septal wall and steer into the ventricle. The delivery guide sheath 400 may be steerable (either one-way steerable within a single plane, or two-way steerable in two planes, such as perpendicular planes) to guide and deliver the remaining devices and systems therein to a desired anatomical site, such as a heart (and, more particularly, in the example of an embodiment of an environment illustrated in FIG. 1, a mitral valve). A delivery catheter 300 may extend distally from and out of the delivery guide sheath 400 to deliver devices and/or systems to the anatomical site to be treated. The delivery catheter 300 thus preferably is generally steerable to position such devices and/or systems relative to an anatomical site as desired for and/or indicated by the procedure or treatment. For instance, in the illustrated example of an embodiment, the delivery catheter 300 is steerable to be substantially centered above the mitral valve MV. The delivery catheter 300 may be formed with articulations and coupled with a one-way or two-way steering mechanism such as known to those of ordinary skill in the art, the details of which do not limit the scope of the present disclosure. An optional device catheter 200 and the inner steerable member 100 (extending through the optional device catheter 200) are configured to move axially (e.g., telescope) with respect to the delivery catheter 300, such as to extend distally out of the delivery catheter 300 to deliver and/or deploy a device or system to an anatomical site. The device catheter 200 and the inner steerable member 100 may be retractable into the delivery catheter 300 to be withdrawn once the procedure has been completed.

As noted above, the example of an embodiment of a system 1000 illustrated in FIG. 1 includes systems and devices for repairing a heart valve, such as repairing leaflet function of a heart valve. In the illustrated example of an embodiment, the device catheter 200 delivers a system such as a leaflet clip spreader 210 having a spreader arm 212 which may grasp a heart valve leaflet L (as illustrated) to clamp a device such as a leaflet clip 220 thereto. Such device catheter 200 may alternately be referenced as a grasper shaft 200 for the sake of convenience and without intent to limit. The illustrated example of an embodiment of an inner steerable member 100 delivers an implant delivery system, such as an anchor garage 110 (e.g., carried by the distal end 101 of the inner steerable member 100), within which an implantable device is delivered to the anatomical site. The distal end 101 of the inner steerable member 100 may be coupled with (e.g., mounted in a counterbore within) a proximal end 113 of the anchor garage 510. In the illustrated example of an embodiment, a stylet 500 extends translatably through the anchor garage 110, and out the distal end 111 of the anchor garage 510, to deploy an implantable device, such as anchor 510, carried at a distal end 501 of the stylet 500. Optionally, the stylet 500 controls delivery of the anchor 510 with respect to the leaflet clip 220 to apply tension thereto via an artificial chordae tendineae 530. The stylet 500 may also be used to control an artificial chordae tendineae tensioning and locking device 520 to adjust the tension of an artificial chordae tendineae 530 extending between the anchor 510 and the leaflet clip 220, and/or to release the anchor 510 from the anchor garage 110.

As may be readily appreciated by those of ordinary skill in the art, the force vector of the artificial chordae tendineae 530 on the leaflet clip 220 is selected and set to effect the desired repair of the heart valve leaflet L to which the artificial chordae tendineae 530 is coupled, such as to achieve the desired closure of such heart valve leaflet L with respect to the other heart valve leaflets. The direction of the force vector of the artificial chordae tendineae 530 is generally determined by the position in which the anchor 510 is implanted in the ventricle V (e.g., within papillary muscle tissue thereof). Accordingly, it is important to be able to accurately control steering of the inner steerable member 100 to implant the anchor 510 in the desired location to effect the desired force vector on the leaflet L via the artificial chordae tendineae 530 coupled between the anchor 510 and the leaflet clip 220.

In accordance with various principles of the present disclosure, a steering mechanism 120 is operatively associated with the inner steerable member 100 to allow unimpeded steering of the inner steerable member 100, such as out of a delivery plane of a delivery catheter 300 through which the inner steerable member 100 is delivered. Examples of embodiments of steering mechanisms 120 formed in accordance with various principles of the present disclosure may be appreciated with reference to FIG. 2, FIG. 3, FIG. 4 (oriented in an opposite direction from which the steering mechanism 120 would be oriented in FIG. 1) and FIG. 5. The illustrated examples of embodiments of steering mechanisms 120 are associated with a distal steerable region 102 of the inner steerable member 100, extending proximally from the distal end 101 of the steerable member 100, though other placements or associations are within the scope and spirit of the present disclosure.

In accordance with various principles of the present disclosure, navigation (e.g., bending) of a steerable region 102 of the inner steerable member 100 is controlled by/with a distal portion 122 of the steering mechanism 120. The distal portion 122 of the steering mechanism 120 is operatively associated with the steerable region 102 of the inner steerable member 100 to impart movement thereto. For instance, the distal portion 122 of the steering mechanism 120 is substantially fixed radially and longitudinally to at least a portion of the steerable region 102 of the inner steerable member 100 so that proximal movement of the steering mechanism 120 causes the steerable region 102 to bend (e.g., towards the location at which the steering mechanism 120 is fixed to the steerable region 102). In contrast, the proximal portion 124 of the steering mechanism 120 is not radially fixed with respect to the proximal portion 104 of the inner steerable member 100 (proximal to the proximal end 103 of the steerable region 102 where the inner steerable member 100 is caused to bend by the steering mechanism 120, as illustrated in FIG. 1). For instance, the proximal portion 124 of the steering mechanism 120 is substantially free-floating within a lumen 105 defined within the inner steerable member 100, and is capable of being moved with respect to the proximal portion 104 of the inner steerable member 100 and at least radially independently of the steerable region 102. Accordingly, longitudinal movement (such as pulling) of the steering mechanism 120 causes movement (e.g., steering, bending, etc.) of the steerable region 102, but radial movement of the generally free-floating proximal portion 124 of the steering mechanism 120 (such as to align with the inner radial portion of a bend in the inner steerable member 100 through which the steering mechanism 120 extends) does not cause radial movement or torquing of the steerable region 102. Accordingly, the proximal portion 124 of the steering mechanism 120 may freely move (e.g., radially) with respect to proximal portion 104 of the inner steerable member 100, such as to follow a bend 303 in the delivery catheter 300 which delivers the inner steerable member 100 (and which thus imparts a corresponding bend to the inner steerable member 100). Thus, the proximal portion 124 of the steering mechanism 120 is free to follow the shortest path of a bend in the inner steerable member 100 (e.g., to be drawn to the inner radial portion of the bend) proximal to the steerable region 102 without reorienting or otherwise affecting the position of the steerable region 102 of the inner steerable member 100. The steerable region 102 is thus steerable to a particular treatment site independently of the steering and orientation of a delivery catheter 300 which delivers the inner steerable member 100 to the general vicinity of the treatment site.

A distal portion 122 of a steering mechanism 120 may be operatively engaged with an inner steerable member 100 in any desired manner which allows the steering mechanism 120 to control movement of the steerable region 102 of the inner steerable member 100 without being affected by movement of a proximal portion 124 of the steering mechanism 120 proximal to the steerable region 102. For instance, a portion of the steering mechanism 120 may be coupled to the wall of the inner steerable member 100 along which the steerable region 102 is formed, with a more proximal portion of the steering mechanism 120 free to move radially with respect to the inner steerable member 100 to move as the inner steerable member 100 bends without affecting the position of the steerable region 102. The steering mechanism 120 may be coupled to an outer surface of, an inner surface of, or within the wall of the inner steerable member 100. If coupled to an outer surface of the steerable region 102, the steering mechanism 120 extends through the wall of the inner steerable member 100 and into the interior of the inner steerable member 100 to be radially movable with respect to the inner steerable member 100.

In accordance with various principles of the present disclosure, a steering mechanism 120 may be associated with a reinforcing layer 130 of the inner steerable member 100, although other configurations are within the scope and spirit of the present disclosure. For instance, in embodiments of inner steerable members 100 without inner reinforcing layers, a steering mechanism 120 may be positioned within the wall of the inner steerable member 100, or may be coupled to an inner surface of the inner steerable member 100, or may be coupled to an outer surface of the inner steerable member 100 and extend through the wall of the inner steerable member 100 into the interior of the inner steerable member 100, such as to be free-floating within the lumen 105 defined by within the inner steerable member 100.

In the examples of embodiments of steering mechanisms 120 illustrated in FIG. 2, FIG. 3, FIG. 4, and FIG. 5, a distal portion 122 of the steering mechanism 120 is operatively associated with an inner steerable member 100 by being operatively associated with a longitudinal extent of a reinforcing layer 130 provided between an outer layer or jacket 140 and an inner layer or liner 150 of the inner steerable member 100. The longitudinal extent of the distal portion 122 of the steering mechanism 120 may define the longitudinal extent of the steerable region 102. The longitudinal extent of the steerable region 102 may be determined by the bend radius desired to be achieved upon actuating the steering mechanism 120. For instance, if a 1.5" bend radius is desired, then the steerable region 102 may be formed to be 3" long. The proximal portion 124 of the steering mechanism 120 is not operatively associated with the inner steerable member 100 or the reinforcing layer 130 thereof, and extends proximally through the lumen 135 of the reinforcing layer 130 and freely within the inner steerable member 100 for unimpeded movement therein (e.g., within the lumen 105 defined by a tubular wall of the inner steerable member 100). The steering mechanism 120 transitions from the proximal portion 124 thereof (operatively associated with the reinforcing layer 130 along the steerable region 102 of the inner steerable member 100) radially inwardly along a transition portion 127 thereof (along the proximal end 103 of the steerable region 102) to the distal portion 122 thereof (movable at least radially independently of the proximal portion 104 of the inner steerable member 100).

Figures 3, 4:
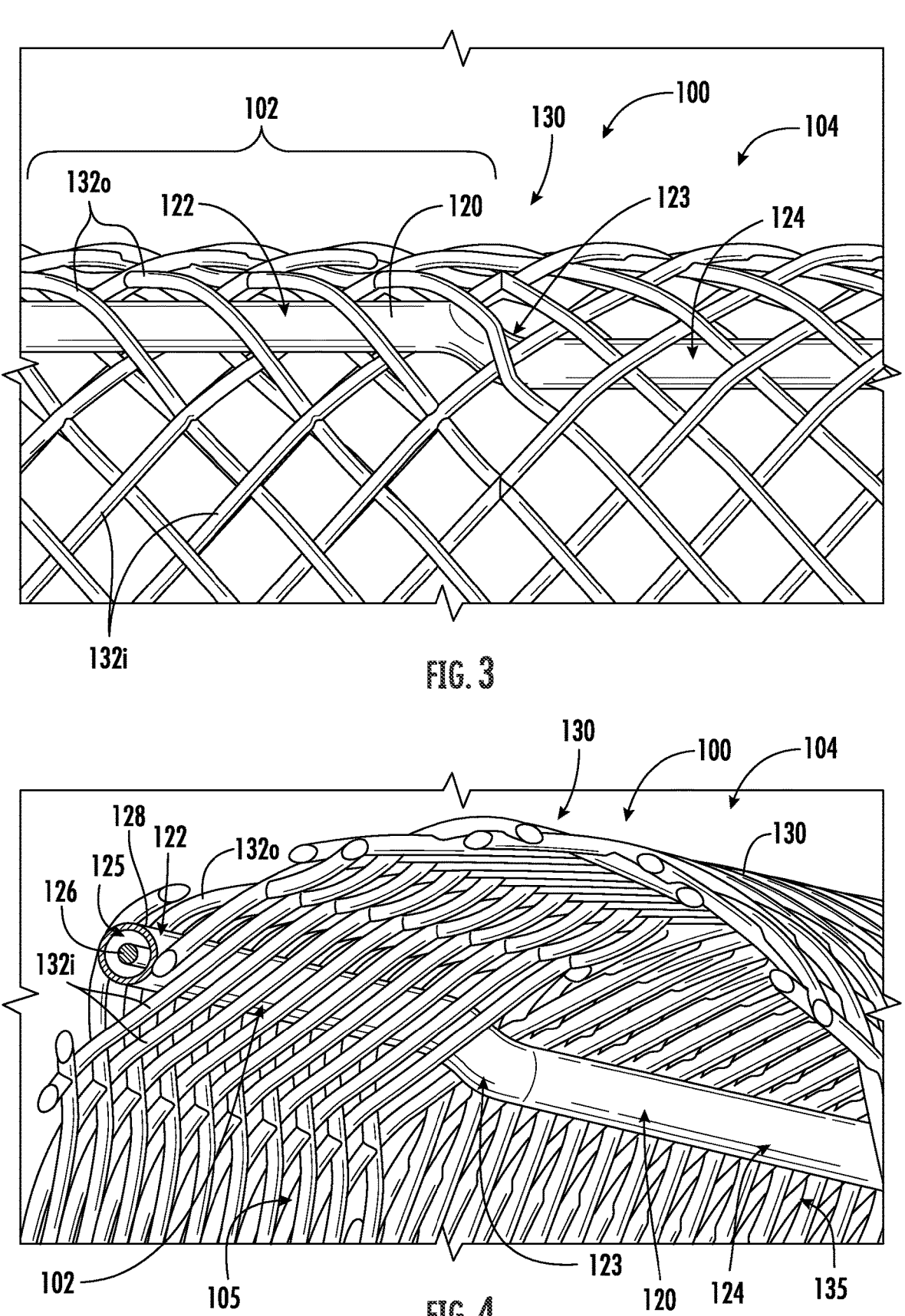
FIG. 3 illustrates an outer perspective detail view of a steerable flexible tubular elongate member with a steering mechanism operatively associated with a reinforcing layer of the steerable flexible tubular elongate member in accordance with various principles of the present disclosure.
FIG. 4 illustrates an inner perspective detail view of a steerable flexible tubular elongate member with a steering mechanism operatively associated with a reinforcing layer of the steerable flexible tubular elongate member in accordance with various principles of the present disclosure.
Figure 5:
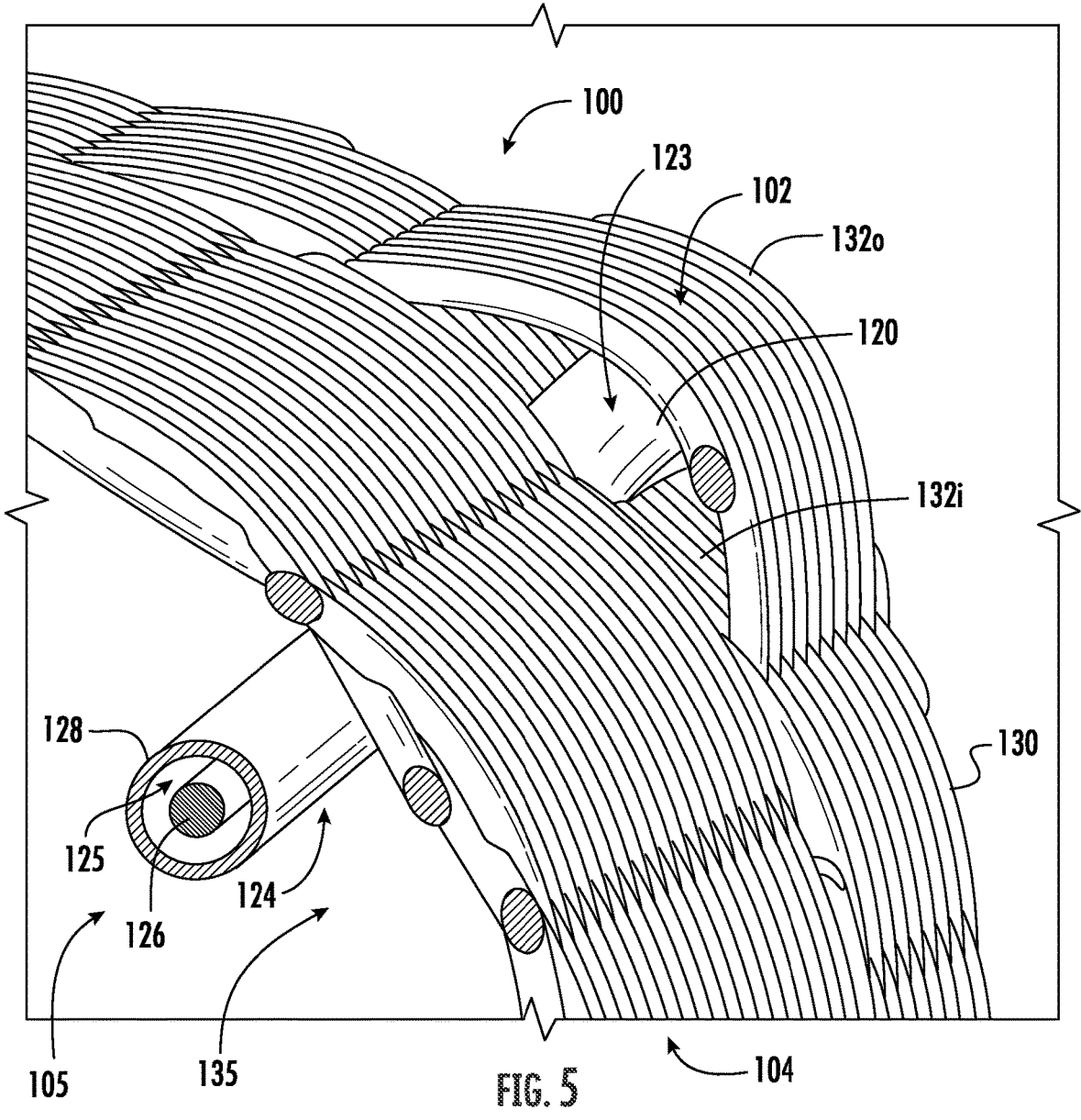
FIG. 5 illustrates an outer and partially cross-sectional detail view of a steerable flexible tubular elongate member formed in accordance with various principles of the present disclosure.

A steering mechanism 120 formed in accordance with various principles of the present disclosure may be operatively associated with the inner steerable member 100, such as with the reinforcing layer 130 thereof, in any of a variety of manners. For instance, in some embodiments, the reinforcing layer 130 is formed with one or more filaments 132. The steering mechanism 120 may be operatively associated with the filaments 132 forming the reinforcing layer 130. The filaments 132 of the reinforcing layer 130 may extend longitudinally and/or circumferentially around the inner steerable member 100. In the example of an embodiment illustrated in FIG. 2, the reinforcing layer 130 includes one or more coupling filaments 134 configured and arranged to couple the steering mechanism 120 with the reinforcing layer 130. In some embodiments, the filaments 132 of the reinforcing layer 130 are braided, interengaged, intertwined, interwoven, knitted, knotted, looped (e.g., bobbinet-style), weaved, woven, wrapped, etc., or the like, such terms (and other grammatical forms thereof) being used interchangeably herein without intent to limit. In such embodiment, the steering mechanism 120 may be operatively associated with the filaments 132 of the reinforcing layer 130 in any of a variety of manners. For instance, the steering mechanism 120 may be interwoven with braided filaments 132 of a reinforcing layer 130, such as in the examples of embodiments illustrated in FIG. 3, FIG. 4, and FIG. 5. For instance, the steering mechanism 120 may be interwoven with the filaments 132 of the reinforcing layer 130, such as woven through a braid of filaments 132, such as illustrated in FIG. 3, FIG. 4, and FIG. 5. More particularly, the steering mechanism 120 may be interwoven within a braided reinforcing layer 130 with outer filaments 132o of the braid over the steering mechanism 120 (radially outwardly, closer to the outer layer 140 of the steerable member 100) and inner filaments 132i under the steering mechanism 120 (radially inwardly, closer to the inner layer 150 of the steerable member 100).

As may be readily appreciated with reference to the examples of embodiments illustrated in FIG. 4 and FIG. 5, the steering mechanism 120 is only operatively associated with, to steer and move with, the steerable region 102 of the inner steerable member 100. The proximal portion 124 of the steering mechanism 120 is positioned within the lumen 105 of the inner steerable member 100 to be relatively freely movable with respect to the proximal portion 104 of the inner steerable member 100 (without imparting movement thereto). However, other placements and configurations are within the scope and spirit of the present disclosure to allow the steering mechanism 120 to be moved radially independently of the configuration of the inner steerable member 100 proximal to the steerable region 102, such as created or caused by tubular members within which the inner steerable member 100 is positioned. As such, the proximal portion 124 of the steering mechanism 120 is able to move without affecting the position of the steerable region 102 of the inner steerable member 100. The steering mechanism 120 thus remains in the desired position for steering to the desired anatomical site at which an operation is to be performed by or with the inner steerable member 100 (e.g., delivery, deployment, and implantation of an implantable device such as an anchor 510). The inner steerable member 100 may thus be considered a steerable deployment/delivery system.

In accordance with various principles of the present disclosure, a steering mechanism 120 may advantageously be a two-part steering mechanism 120 having a pull element 126 (e.g., a pull wire 126) within a lumen 125 defined within an outer sheath 128. Such configuration allows the distal portion 122 of the steering mechanism 120 to be coupled with the steerable region 102 yet also allows a portion of the steering mechanism 120 to move with respect to the steerable region 102 to steer the steerable region 102. For instance, the outer sheath 128 may be coupled to the steerable region 102 of the inner steerable member 100 (e.g., bonded, interwoven, or otherwise coupled with filaments 132 of a reinforcing layer 130 of the inner steerable member 100) with only a portion of the pull wire 126 fixed to a portion of the outer sheath 128. In some embodiments, only the distal end of the pull wire 126 is coupled (in any desired manner) to the outer sheath 128. The combined outer sheath 128 and inner pull wire 126 are free of attachment to the inner steerable member 100 along a proximal portion 124 of the steering mechanism 120 to allow independent movement of the pull mechanism 120 (at least radially) as described above. In some embodiments, the outer sheath 128 of a two-part steering mechanism 120 has an outer diameter of at least approximately 0.022"±0.002" (0.559 mm±0.051 mm) and in inner diameter of approximately 0.020"±0.001" (0.508 mm±0.02 mm) to allow a pull wire 126 to be routed therethrough and to be readily axially translatable therein along the longitudinal axis LA of the inner steerable member 100. The steerable member 100 of such embodiment may have an outer diameter of approximately 0.08"±0.02" (2.03 mm±0.5 mm) up to approximately 0.3"±0.02" (7.62 mm±0.5 mm).

In embodiments in which the steering mechanism 120 is operatively engaged with a reinforcing layer 130 of an inner steerable member 100, such as illustrated in FIG. 2, FIG. 3, FIG. 4, and FIG. 5, the steering mechanism 120 may be operatively engaged with the inner steerable member 100 during manufacture of the reinforcing layer 130 in a variety of manners. An inner steerable member 100 may be formed in accordance with various principles of the present disclosure with a reinforcing layer 130 provided or formed between an outer layer 140 and an inner layer 150. The inner layer 150, which may also be known as a liner, may be made of a lubricious material to facilitate insertion and transport of medical devices therein and therethrough. Such inner layer 150 may be formed of a material such as, but not limited to, polytetrafluoroethylene (PTFE), tetrafluoroethylene with perfluoroalkyl vinyl ether (PFA), perfluoropropyl vinyl ether, perfluoromethyl vinyl ether, fluorinated ethylene pro-pylene (FEP), polyether block amide (PEBA), polyurethane, nylon, or copolymers or blends thereof. The inner layer 150 may be formed in a variety of manners, such as an extrusion process, or by molding or coating a material over a mandrel or within another layer (a relatively outer layer) of the flexible tubular elongate member. The outer layer 140, which may be known as a jacket, may be formed of a generally lubricious material providing the inner steerable member 100 with a frictionless (or at least reduced friction) biocompatible outer surface to facilitate maneuvering of the inner steerable member 100 within the flexible tubular elongate member 200 in which it extends, and/or within passageways/lumens of a patient's body without damaging the flexible tubular elongate member 200/surrounding tis-sue. Such outer layer 140 may be formed of any of a variety of biocompatible materials, such as nylon, polyurethane, polyether block amide (PEBA), PTFE, high density poly-ethylene (HDPE), liquid crystal polymer (LCP), or copoly-mers or blends thereof, in any of a desired manners, such as extrusion, dipping, painting, brush coating, spraying, mold-ing, etc., the coating material over the other layers of the flexible tubular elongate member. It will be appreciated that the inner steerable member 100 may have differing charac-teristics (e.g., flexibility, stiffness, wall thickness, elasticity, durometer, etc.) along the length thereof.

The reinforcing layer 130 may be configured to impart one or more properties or characteristics to the inner steer-able member 100, such as strength, flexibility (or a desired degree of stiffness), enhanced maneuverability, tensile strength, torque transmission abilities, steering capabilities, stability, durability, elasticity, resistance to fracture, etc., such as to give the inner steerable member 100 various abilities needed for navigating within a complex system such as the multi-catheter stack-up assembly 1000 and/or within the body, delivering a device or system or treatment or therapy, implanting a device or system, manipulating a device or system, etc., or otherwise selected for an intended use of the inner steerable member 100. It will be appreciated that not all properties or characteristics of the reinforcing layer 130 may be considered to "reinforce", and reference to and use of the term reinforce, and other grammatical forms thereof, herein is for the sake of convenience and not necessarily limited to traditional concepts of "reinforcing."

The reinforcing layer 130 of an inner steerable member 100 formed in accordance with various principles of the present disclosure may be formed over the inner layer 150, or formed independently with the material of the inner layer 150 applied thereto to form the inner layer 150. In some embodiments, the reinforcing layer 130 may be embedded into the inner layer 150. In some embodiments, the outer layer 140 is provided over the reinforcing layer 130, such as to enclose or encapsulate the reinforcing layer 130 within the wall of the inner steerable member 100. The outer layer 140 may fill voids or gaps in the reinforcing layer 130, such as to embed the reinforcing layer 130 within the outer layer 140 and/or to form a sandwich-like structure comprising the inner layer 150, the reinforcing layer 130, and the outer layer 140.

The reinforcing layer 130 may be formed, shaped, and configured in any of a desired configurations to provide or impart a desired property to the inner steerable member 100 along the length thereof (extended along a longitudinal axis thereof) and/or along a portion of the circumference of the flexible tubular elongate member (about the longitudinal axis thereof), as well as to allow the steering mechanism 120 to be operatively associated therewith. In some embodi-ments, the reinforcing layer 130 is formed of a plurality of elongated elements 132 (filaments, fibers, strands, ribbons, etc., referenced herein as filaments for the sake of conve-nience and without intent to limit), such as wires, which extend longitudinally along the length of the inner steerable member 100. The filaments 132 may be formed of any of a variety of materials, such as a metal, a metal alloy (stainless steel, a nickel-titanium alloy or other nickel alloy, aa tung-sten alloy, a chromium alloy, etc.), a polymer, a metal-polymer composite material, etc., without limitation. The filaments 132 may be formed of a linear elastic or non-super-elastic of super-elastic or shape-memory material, such as selected based on the intended use of the inner steerable member 100. The filaments 132 may have any of a variety of cross-sectional shapes, such as to impart a desired characteristic or property to the reinforcing layer 130. The diameter or thickness of the filaments 132 is selected based on the intended use of the inner steerable member 100 to result in an inner steerable member 100 with a desired overall diameter as well as a desired wall thick-ness. At least a portion of the reinforcing layer 130 may be coated, such as with a polymeric coating material, to impart a desired further property or characteristic to one or more filaments 132 of the reinforcing layer 132. Such coating may be applied in any of a desired manners, such as extrusion (e.g., over each filament), dipping, painting, brush coating, spraying, etc., without intent to limit.

In some embodiments, the filaments 132 (singly or in pairs or in groups of more than two filaments 132) are braided with other filaments 132 (singly or in pairs or in groups of more than two filaments 132), in any of a variety of patterns, the specifics of which are not critical to the present disclosure. It will be appreciated that reference may be made interchangeably herein to terms such as braided, interengaged, intertwined, interwoven, knitted, knotted, looped (e.g., bobbinet-style), overlapped, weaved, woven, wrapped, etc. (including various grammatical forms thereof), without intent to limit.

In accordance with various principles of the present disclosure, the steering mechanism 120 (such as in the form of a pull mechanism 120) may be interwoven into a distal portion of the reinforcing layer 130, such as by being woven with the woven filaments 132 thereof. Once the desired length of the reinforcing layer 130 for the steerable region 102 is formed, the steering mechanism 120 may be with-drawn from the braiding process and from the filaments 132 of the reinforcing layer 130. For instance, the braiding process by which the reinforcing layer 130 is being formed may be paused, and the steering mechanism 120 may be diverted from (e.g., pulled out of alignment with or other-wise withdrawn from) the reinforcing layer 130. If the reinforcing layer 130 is formed over an already-formed inner layer 150, then the inner layer 150 may be breached, e.g., punctured (such as with an instrument such as a scalpel) to allow the steering mechanism 120 to be extended or positioned within the lumen 135 of the reinforcing layer 130 and the interior of (e.g., lumen 105 within) the inner steerable member 100.

In view of the above, an inner steerable member 100 formed in accordance with various principles of the present disclosure with a steering mechanism 120 having a free-floating proximal portion 124, proximal to the steerable region 102 of the inner steerable member 100, allows the steerable region 102 to be maneuvered out of a plane in which the inner steerable member 100 may be bent (e.g., by virtue of bends in one or more flexible tubular elongate members in which the inner steerable member 100 extends). In some examples, it may be desirable to steer the inner steerable member 100 in a different plane than that of the one or more outer flexible tubular elongate members 200, 300, 400 in which the inner steerable member 100 extends and is delivered to the treatment site. An example of a desired position of the inner steerable member 100 within the heart H to is illustrated in FIG. 1. Various therapies performed on regions of the heart H, such as the heart valve, may require access to heart tissue at a location underneath the leaflets L of the valve. However, the devices and systems delivered transluminally to the heart valve, such as through the septal wall, may be in a position which does not readily facilitate maneuvering of repair devices and systems out of the plane in which the delivery catheter 300 for such devices and systems extends. Repair of heart valves such as the mitral valve MV, such as to restore proper functioning of the valve such as to treat (and to prevent potentially fatal results of) conditions such as mitral valve regurgitation, may involve extending artificial chordae tendineae 530 from the leaflet L to an anchor 510 positioned on the ventricle wall V underneath the leaflet L, such as underneath the posterior leaflet of the mitral valve MV Such position on the ventricle wall V generally does not lie within or otherwise intersect the plane in which the delivery system 1000 extends to deliver the inner steerable member 100 used to deliver the anchor 510. Moreover, the configuration of the system 1000 and delivery catheter 300 within a delivery plane generally constrain movement of the delivered devices and systems to within such delivery plane. An inner steerable member 100 formed in accordance with various principles of the present disclosure may be telescoped out of the delivery catheter 300 and then may be steered out of the delivery plane, anywhere between 0 degrees and 180 degrees, such as, without limitation, 45 degrees or 90 degrees or 135 degrees, and into a second plane (e.g., transverse or perpendicular to the delivery plane), in which the inner steerable member 100 may then be steered, as shown in FIG. 1.

It will be appreciated that a steerable member 100 formed in accordance with various principles of the present disclosure may deliver and/or deploy devices other than anchors, with or without a delivery device such as an anchor garage 110. For instance, the delivery catheter 100 may deliver a device on its own without the need for a further device such as a stylet 500 as in the example of an embodiment illustrated in FIG. 1. Moreover, it will be appreciated that principles of the present disclosure may be applied to devices and systems other than for mitral valve repair, such as in other areas of the cardiovascular system. Proper positioning of a steerable member delivered through another steerable tubular member may be desired in a variety of other anatomical areas or systems, such as the gastrointestinal and/or digestive system, the abdominal cavity, the urinary tract, the reproductive tract, the respiratory system, circulatory system, etc. The disclosed medical devices and systems may also be inserted via different access points and approaches, e.g., percutaneously, endoscopically, laparoscopically, or combinations thereof. Various further benefits of the various aspects, features, components, and structures of a steerable member such as described above, in addition to those discussed above, may be appreciated by those of ordinary skill in the art.

It is to be understood by one of ordinary skill in the art that the present discussion is a description of illustrative examples of embodiments only, and is not intended as limiting the broader aspects of the present disclosure. All apparatuses and methods discussed herein are examples of apparatuses and/or methods implemented in accordance with one or more principles of the present disclosure. These examples are not the only way to implement these principles but are merely examples, not intended as limiting the broader aspects of the present disclosure. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

As used herein, the singular forms "a," "an," and "the" are intended to include the plural forms as well, unless the context clearly indicates otherwise. As used in this specification and the appended claims, the term "or" is generally employed in its sense including "and/or" unless the content clearly dictates otherwise. As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise. The terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, engaged, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements, components, features, regions, integers, steps, operations, etc. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A steerable system for accessing an anatomical site within a patient's body, said steerable system comprising:

an elongate member having a steerable region along a portion thereof;

wherein the elongate member includes an inner layer, an outer layer, and a reinforcing layer disposed between the inner layer and the outer layer;

a steering mechanism having a distal portion operatively associated with said steerable region to effect movement of said steerable region, and a proximal portion axially and radially movable with respect to said steerable region;

wherein the distal portion of the steering mechanism is interwoven with the reinforcing layer; and wherein the proximal portion of the steering mechanism is disposed radially inward of the reinforcing layer.

2. The steerable system of claim 1, wherein said distal portion of said steering mechanism is embedded within a distal portion of said elongate member.

3. The steerable system of claim 2, wherein:

said steering mechanism comprises a two-part pull mechanism with an inner pull wire axially movable within an outer sheath;

a portion of said outer sheath is fixed with respect to said steerable region of said elongate member; and a distal end of said pull wire is coupled to said outer sheath such that axial movement of said pull wire steers said outer sheath.

4. The steerable system of claim 1, wherein:

said elongate member has a tubular wall defining a lumen therein;

said distal portion of said steering mechanism is operatively associated with said tubular wall of said flexible elongate member along said steerable region to steer said steerable region; and said proximal portion of said steering mechanism extends within the lumen defined by said tubular wall of said elongate member and is movable radially-independently of said steerable region.

5. The steerable system of claim 1, wherein:

said steering mechanism comprises a two-part pull mechanism with an inner pull wire axially movable within an outer sheath;

a portion of said outer sheath is operatively associated with filaments of said reinforcing layer along said steerable region; and a distal end of said pull wire is coupled to said outer sheath such that axial movement of said pull wire steers said steerable region.

6. The steerable system of claim 5, wherein said portion of said outer sheath operatively associated with said filaments along said steerable region is fixed with respect to said steerable region.

7. The steerable system of claim 1, wherein a distal end of said steering mechanism is fixed with respect to said steerable region.

8. A steerable system comprising:

at least one steerable tubular member;

an inner steerable member extending through and along said at least one steerable tubular member and having a steerable portion along a distal end thereof;

wherein the inner steerable member includes an inner layer, an outer layer, and a reinforcing layer disposed between the inner layer and the outer layer;

a steering mechanism having a distal portion operatively associated with said steerable region of said inner steerable member to effect movement of said steerable region, and a proximal portion radially movable with respect to said steerable region;

wherein the steering mechanism includes a distal portion interwoven with the reinforcing member, a medial portion that dives in through the reinforcing layer, and a proximal portion extending along an inner surface of the reinforcing layer; and wherein said at least one steerable tubular member is steered within a first plane and said steering mechanism is operatively associated with said inner steerable member to steer said inner steerable member in a second plane transverse to the first plane.

9. The steerable system of claim 8, wherein:

said at least one steerable tubular member includes a two-way steerable delivery catheter; and said inner steerable member is axially extendable out of a distal end of said two-way steerable delivery catheter and steered by said steering mechanism within the second plane.

10. The steerable system of claim 8, wherein:

said inner steerable member has a tubular wall defining a lumen therein;

said distal portion of said steering mechanism is operatively associated with said tubular wall of said inner steerable member along said steerable region to steer said steerable region; and said proximal portion of said steering mechanism extends within the lumen defined by said tubular wall of said inner steerable member and is movable radially-independently of said steerable region.

11. The steerable system of claim 8, wherein:

said steering mechanism comprises a two-part pull mechanism with an inner pull wire axially movable within an outer sheath;

a portion of said outer sheath is operatively associated with filaments of said reinforcing layer along said steerable region; and a distal end of said pull wire is fixed to said outer sheath such that axial movement of said pull wire steers said steerable region.

12. The steerable system of claim 11, wherein said portion of said outer sheath operatively associated with said filaments along said steerable region is fixed with respect to said steerable region.

13. The steerable system of claim 8, wherein a distal end of said steering mechanism is fixed with respect to said steerable region.

14. A method of navigating a steerable delivery/deployment system with respect to a steerable delivery catheter, said method comprising:

bending the steerable tubular delivery catheter and thus the steerable delivery/deployment system within a first plane to deliver the steerable delivery/deployment system to an area of an anatomical site; and operating a steering mechanism to steer a steerable region of the steerable delivery/deployment system within a second plane transverse to the first plane, the steering mechanism having a distal portion fixed with respect to the steerable region to steer the steerable region, and a proximal portion radially movable with respect to the steerable region to conform to the bend of the steerable delivery catheter in the first plane;

wherein the steerable tubular delivery catheter includes an inner layer, an outer layer, and a reinforcing layer disposed between the inner layer and the outer layer; and wherein the steering mechanism includes a distal portion interwoven with the reinforcing member, a medial portion that dives in through the reinforcing layer, and a proximal portion extending along an inner surface of the reinforcing layer.

15. The method of claim 14, further comprising allowing the proximal portion of the steering mechanism to conform to the bend of the steerable delivery catheter without torquing the steerable region of the steerable delivery/deployment system out of position to be bent in the second plane by the steering mechanism.

* * * * *